United States Patent [19]

Roat et al.

[11] Patent Number: 4,772,735

[45] Date of Patent: Sep. 20, 1988

[54] COORDINATION COMPLEXES OF PLATINUM WITH AMIDES

[75] Inventors: Rosette M. Roat, Chestertown, Md.; Seymour Yolles, Newark, Del.

[73] Assignee: University of Delaware, Newark, Del.

[21] Appl. No.: 899,691

[22] Filed: Aug. 25, 1986

[51] Int. Cl.$^4$ .............................................. C07F 15/00
[52] U.S. Cl. .................................................. 556/136
[58] Field of Search ........................ 556/136; 548/404

[56] References Cited

U.S. PATENT DOCUMENTS

| | | | |
|---|---|---|---|
| 4,151,185 | 4/1979 | Allcock et al. | 556/17 |
| 4,394,319 | 7/1983 | Hydes et al. | 556/137 |
| 4,424,359 | 1/1984 | Kaschig et al. | 526/241 |
| 4,476,305 | 10/1984 | Kvita et al. | 526/262 |
| 4,582,881 | 4/1986 | Kvita et al. | 525/326.7 |
| 4,732,893 | 3/1988 | Pasini et al. | 556/137 |

OTHER PUBLICATIONS

Roat et al., "Oxidative Reactions of Potassium Tetra-chloroplatinate (II) with N,N-dialkylacetamides Under Mild Conditions", Chem. Abs. 105:115194v, (1986).
Barton et al., "The Other Platinum Blues, An X-ray Photoelectron Study", Amercian Chem. Soc., (1978).
Umberto Belluco, "Organometallic & Coordination Chemistry of Platinum", Academic Press, pp. 95–208, (1974).

Primary Examiner—Anthony McFarlane
Attorney, Agent, or Firm—Dean R. Rexford

[57] ABSTRACT

Disclosed are platinum(IV) chelates derived from substituted amides. The chelates result from the reaction under mild conditions of potassium chloroplatinate(II) and the appropriate amide. The chelate trans-dichloro-cis-bis(dimethylacetamide-C,O) was prepared, fully characterized and exemplified in preparation of the antihistamine diphenhydramine hydrochloride.

6 Claims, 3 Drawing Sheets

Reflectance Infrared Neat Solid Pt(C_4H_8NO)_2Cl_2

COORDINATION COMPLEXES OF PLATINUM WITH AMIDES

BACKGROUND OF THE INVENTION

1. Field of the Invention

The invention relates to new platinum(IV) coordination complexes with alkyl amides and preparation of them from potassium tetrachloroplatinate(II) and dialkylacetamides by way of oxidative addition under mild reaction conditions. The product of the reaction starting with dimethylacetamide as an amide ligand was used in a new route for the preparation of a complicated aromatic N-substituted acetamide, an important intermediate in the preparation of antihistamines (diphenhydramine hydrochloride).

2. Prior Art and Objectives

The importance of coordination compounds and organometallic compounds has increased substantially in recent years with the proliferation of uses of these compounds as catalysts and therapeutic agents. Many of the chemical processes in which coordination compounds are employed are truly catalytic; that is, they are accelerated by very small quantities of the compound which can be recovered virtually unchanged after completion of the reaction. On the other hand, metal complexes are employed in reactions where they serve as starting materials for compounds that cannot otherwise be readily produced, changed in the process, or are not a constituent of the product, so that the metal can be recovered after completion of the reaction. In metal complexes employed as therapeutic agents, a high degree of specificity exists, but as a result of the high level of interest in this field, those highly skilled can determine the biochemical efficacy of a compound from its composition, structure, and physical properties.

To appreciate the means whereby the composition and structure of the complex can be varied within the general framework, a review of the basic structure is useful. Coordinating or complexing Lewis bases (electron pair donors) called ligands react with metals (usually heavy metals) or metal ions. The geometric configuration of the complex depends upon the nature of the ligand, including the total number of atoms and the number of donor atoms on each ligand. The position of a ligand with respect to its attachment to the central atom (i.e., cis or trans) may be varied. This can affect the complex's stability and functionality in chemical and therapeutic applications. Coordination compounds are often categorized in terms of the rate in which they undergo substitution or loss of ligands.

Notwithstanding its high cost as a scarce precious metal, complexes of platinum are extensively used chemically and therapeutically. In the latter use, the anticancer properties of cis-dichlorodiammine platinum(II) (cis-Pta$_2$Cl$_2$) are well known. This heavy metal complex containing a central atom of platinum surrounded by two chloride atoms and two ammine ligands (in the cis position with a square-planar configuration) is widely used in human cancer chemotherapy. Many variations from this structure and composition have been synthesized and evaluated in an effort to understand the mechanism of action and to develop a cure for the disease.

Practitioners, by selection from a variety of ligands for platinum complexes, have synthesized and evaluated many compounds for efficacy as anticancer agents. In the literature, B. Rosenberg, *Naturwissenschaften* 60, 399, (1973), summarized the relationship of structure and activity for platinum compounds. From this summary, certain generalizations can be drawn:

active compounds exchange only some of their ligands quickly (chloride is fast; amine is slow);

a "window of lability" exists for the leaving ligand (i.e., bracketed between nitrate which is too fast and thiocyanate which is too slow);

active complexes are neutral;

active molecules are of square planar or octahedral geometric structure;

active complexes have two cis leaving groups or one bidentate leaving group; and ligands trans to the leaving group should be strongly bonded.

With these generalities as guidelines, those skilled in the art, with a reasonable degree of certainty, can predict the efficacy of a therapeutic compound. It would be of interest to see if similar guidelines apply to chemical applications.

While a great variety of coordination compounds is possible by choice of ligands, in view of its therapeutic use, much interest is centered on cis-Pta$_2$Cl$_2$ with its ammine ligands. Analogs with ammonia-derived organic ligands could be valuable, chemically as a carrier of the labile nitroge-containing radical for synthesis of difficulty prepared compositions, as well as biochemically through the relationship of the nitrogen-containing radical of amino acid constituents of animal tissue. This latter may help elucidate the selective destruction of cancerous cells by platinum compounds.

In U.S. Pat. No. 4,283,342, issued Aug. 11, 1981, Yolles obtained platinum coordination compounds of quinones by reactions of cis-dichloro platinum(II) in substituted amide solvents.

Accordingly, it is an object of the present invention to prepare novel platinum complexes having nitrogen-containing organic ligands.

It is a further object of the present invention to prepare a platinum complex with amide ligands.

It is yet another objective of the present invention to prepare a difficulty synthesized aromatic derivative of acetamides (N-2-phenylethyl(methyl)acetamide), and the preparation of a class of antihistamines by employing platinum complexes amide ligands and benzyl bromide.

SUMMARY OF THE INVENTION

In accordance with the objectives of the invention, a new platinum complex, trans-dichloro-cis-bis(dimethylacetamido-C,O) platinum(IV) was prepared from dimethyl acetamide and potassium tetrachloroplatinate(II) under mild reaction conditions.

The foregoing new platinum compound was used to prepare a mixed secondary acetamide, a precursor of Benadryl ® (diphenhydramine hydrochloride USP) a widely used medication.

BRIEF DESCRIPTION OF THE DRAWING

The understanding of the invention is facilitated by reference to the drawing in which.

DETAILED DESCRIPTION OF THE INVENTION

Figure 1:
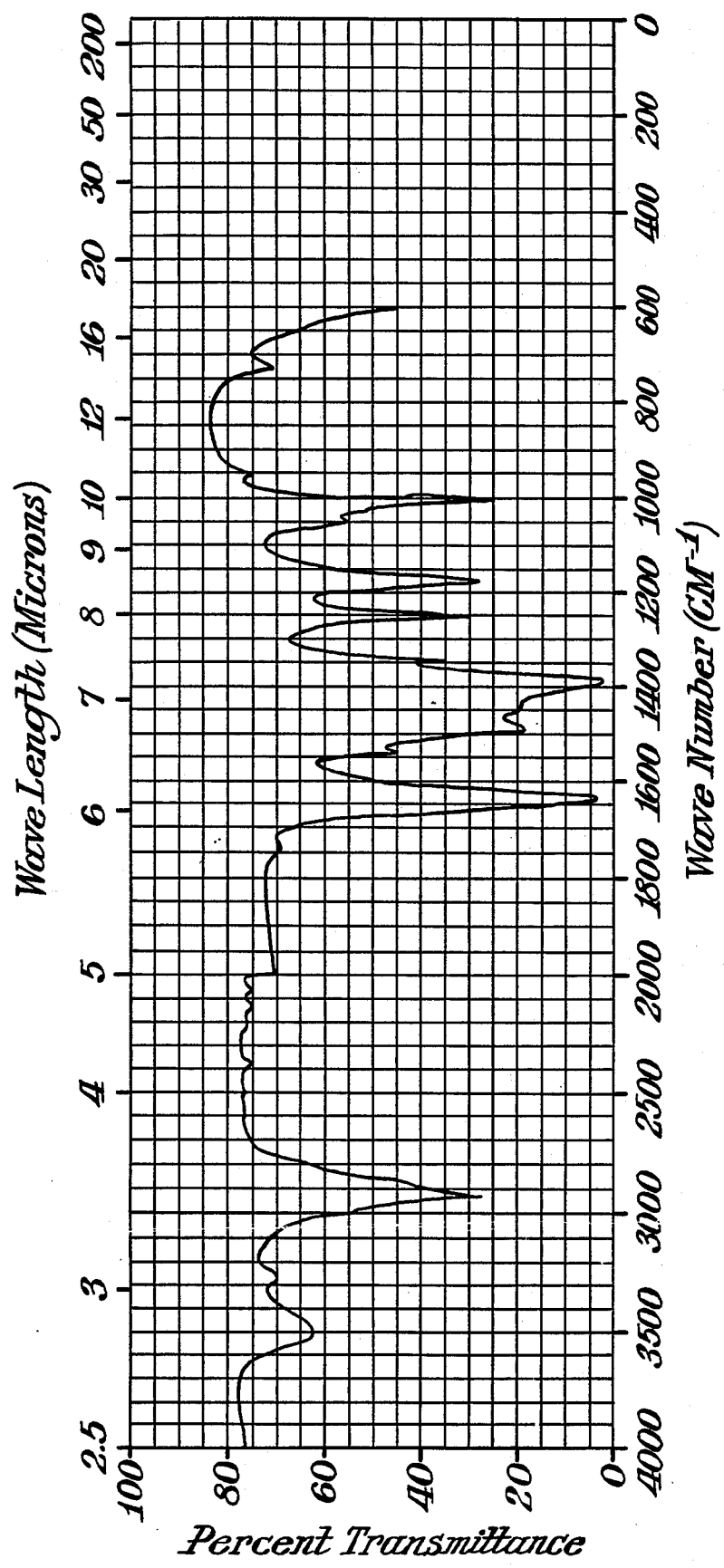
FIG. 1 is a representation of the transmittance infrared spectrum of neat acetamide on a salt plate.

In spite of an earlier interest in reactions of platinum-(II) compounds with acetamides and the complex systems which result, little has been done to prepare and fully characterize chemically, physically, and biologically, platinum(IV) coordination complex systems. The original amide derivative, the blue compound "platinblau," synthesized in 1908, has been variously characterized up until recently (Barton, et al, *Journal of the American Chemical Society* 100, page 3785, 1978) as mixed oxidation state oligomeric compounds containing platinum(II), platinum(III), and platinum(IV) species. Platinum(IV) amide derivatives in this composition were characterized by bonding of the amide ligands through nitrogen and oxygen and not through platinum-carbon bonds. Classically, platinum(IV) alkyl and aryl complexes have been prepared by addition of Grignard or alkyl lithium reagents to platinum(IV) compounds, or by oxidative addition of alkyl and acyl halides or metal halides to platinum(II) compounds. Orthometallation reactions between platinum(II) and aromatic coordinating substituents are known and have been characterized as interactions between carbon-hydrogen groups and metal centers, however, oxidative addition to the centers has not been found or postulated (Brookhart, M. et al., *J. Organomet Chem.* 250, page 395, 1983).

In the present invention, it has been observed that a reaction occurs under mild conditions upon combining potassium tetrachloroplatinate(II) ($K_2PtCl_4$) and at least two-fold molar excess of dimethylacetamide, DMA, $(CH_3C(O)N(CH_3)_2)$ results in a pale yellow crystalline product. On the basis of elemental analysis, X-ray crystallography, $^{13}C$ nuclear magnetic resonance (NMR) spectrometry and infrared (IR) spectroscopy, this novel crystalline compound has been identified as

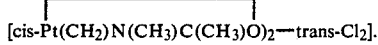

[cis-Pt(CH$_2$)N(CH$_3$)C(CH$_3$)O)$_2$—trans-Cl$_2$].

It results from an oxidative-addition reaction involving C—H bond cleavage and C—Pt bond formation. From the nature of its structure and its oxidation state in this invention, it was expected to have useful properties in chemical synthesis and in biochemistry.

EXPERIMENTAL

Synthesis of

[Pt(CH$_2$N(CH$_3$)C(CH$_3$)O)$_2$Cl$_2$]

Reagent grade dimethylacetamide (DMA), used as received, on IR and NMR analyses showed agreement with literature values. Potassium tetrachloroplatinate(II) ($K_2PtCl_4$), supplied by Johnson Matthey, Inc. was used as received. Reactions were carried out in an inert, dry atmosphere.

To a volume of 80 mL DMA a quantity, 1.0021 g (2.4 mmol) of $K_2PtCl_4$ was added thereby providing an approximate amount of 500 molar excess of DMA to produce a slurry which was heated and stirred at 60° C. until all the $K_2PtCl_4$ had dissolved (approximately 120 hours). The resultant golden yellow solution was centrifuged to remove 0.2333 g (3.3 mmol) of potassium chloride (KCl). The supernatant liquid was then reduced in volume by about two-thirds at reduced pressure until solid product began to form, upon which the supernatant and the solid which started to form were stored at 0° C. for 12 hours. The pale yellow crystals that formed were removed from the supernatant liquid by centrifugation, washed with tetrahydrofuran and dried under vacuum for 12 hours, to provide 0.3392 g (0.77 mmol) of Pt(C$_4$H$_8$NO)$_2$Cl$_2$, a yield of 51.3% based on $K_2PtCl_4$ as the starting material. Elemental analysis resulted in the following percentage composition, with calculated percentages based on Pt(C$_4$H$_8$NO)$_2$ Cl$_2$:

Calculated: C=21.93; H=3.68; N=6.39; Cl=16.18; Pt=44.52. Found: C=21.78; H=3.60; N=6.39; Cl=16.11; Pt=44.45.

Further reduction in volume of the supernatant liquid yielded a small number of darker yellow crystals which were identified by elemental analysis and X-ray diffraction as Pt(C$_4$H$_9$NO)$_2$Cl$_2$.

X-RAY CRYSTALLOGRAPHY

Crystals of Pt(C$_4$H$_8$NO)$_2$Cl$_2$ suitable for X-ray diffraction were obtained by reducing the volume of the $K_2PtCl_4$/dimethyl acetamide reaction supernatant liquid by half and storing the remaining solution at an ambient temperature which after two weeks resulted in separation from the mother liquor of well-formed, pale yellow orthorhombic bipyramids. A crystal having the dimensions 0.36 mm×0.18 mm×0.22 mm was attached to a glass fiber by epoxy cement for mounting in the diffractometer.

Data on this material was collected on a Nicolet R3 diffractometer using graphite-monochromated MoKα radiation. The reflections were collected with an ω (omega) scan technique over a range of 4°–55° in 2 θ (theta). The structure was solved by using the SHELXTL (version 4.1) program system (Nicolet Corporation, Madison WI) to provide bond angles and lengths revealing that platinum was present as platinum-(IV) and was bonded to a carbon atom. These analyses led to the conclusion that the composition was

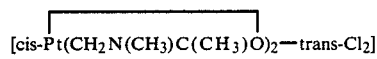

[cis-Pt(CH$_2$N(CH$_3$)C(CH$_3$)O)$_2$—trans-Cl$_2$]

with the structure:

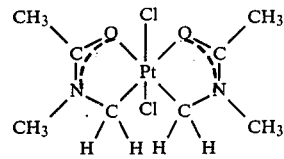

Similar X-ray crystallographic studies were conducted on the second type crystal, much darker yellow in color and more soluble in the supernatant, which was isolated from the same mother liquor and identified by elemental analysis as (C$_4$H$_9$NO)$_2$PtCl$_2$. These X-ray studies indicated a composition with no Pt—C bonds, the acetamide ligands being bonded to the metal center through carbonyl oxygens and situated trans to each other. The structural formula indicated by these studies trans-dichlorobis(dimethylacetamide-O) platinum(II) with the structure:

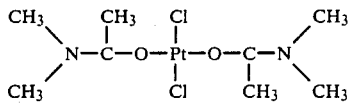

13C NUCLEAR MAGNETIC RESONANCE SPECTRA (NMR)

Appropriate $^{13}C$ NMR spectra of the solid state reaction products of $K_2PtCl_4$ and DMA were obtained on a Bruker CXP300 spectrometer at 75.5 MHz. These spectra revealed resonances of carbon atoms affected by coordination to plainum shifted in two directions: downfield for carbonyl carbon and upfield for methylene carbon bonded to platinum. The downfield shift occurs in this carbon is deshielded. Movement of oxygen electron density towards the platinum metal center explains the deshielding which was observed.

The coupling constant for platinum/methylene carbon interaction was found to be 620±20 Hz. $J_{Pt-C}$ values for sp$^3$ hybridized carbon varies from 360 to 698 H$_z$, depending upon the ligand trans to carbon. The coupling constant increases as the trans influence of the trans ligand decreases in the order:

$CH_3 > CH_2R >\ > Cl > OH$ = ligands trans to Pt—C

Smallest $J_{Pt-c}$         Largest $J_{Pt-C}$

By analogy, it would be expected that a large coupling constant for $(C_4H_8O)_2Cl_2Pt$ in which carbons are trans to oxygen ligands of low trans influence. The methylene carbons are therefore positioned cis to each other, confirming X-ray and infrared data.

INFRARED SPECTROSCOPY

Infrared spectroscopy of the pale yellow compound,

in Nujol mull, CsI pellet and neat solid by reflectance confirmed its structure by the following:

the carbonyl peak of DMA at 1639 cm$^{-1}$ was lowered to 1568 cm$^{-1}$ in both Nujol mull and CsI pellet spectra, an indication of carbonyl oxygen bonding to platinum;

the γ (Pt—Cl) peak was seen in the CsI pellet at 335 cm$^{-1}$ and the reflectance spectrum at 341 cm$^{-1}$, the single frequency indicating transplacement of the chloride ligands;

two stretching frequencies at 618 and 603 cm$^{-1}$ were seen in the region expected for γ (Pt—C) in the CsI pellet spectrum indicating cis placement of the methylene ligands; and a single band at 520 cm$^{-1}$ in the CsI pellet spectrum was assigned to γ (Pt—O) and in the same region in the reflectance spectrum exhibited a broad band between 500 and 550 cm$^{-1}$. These latter were an indication of Pt—O bonds in the cis configuration.

Figure 2:
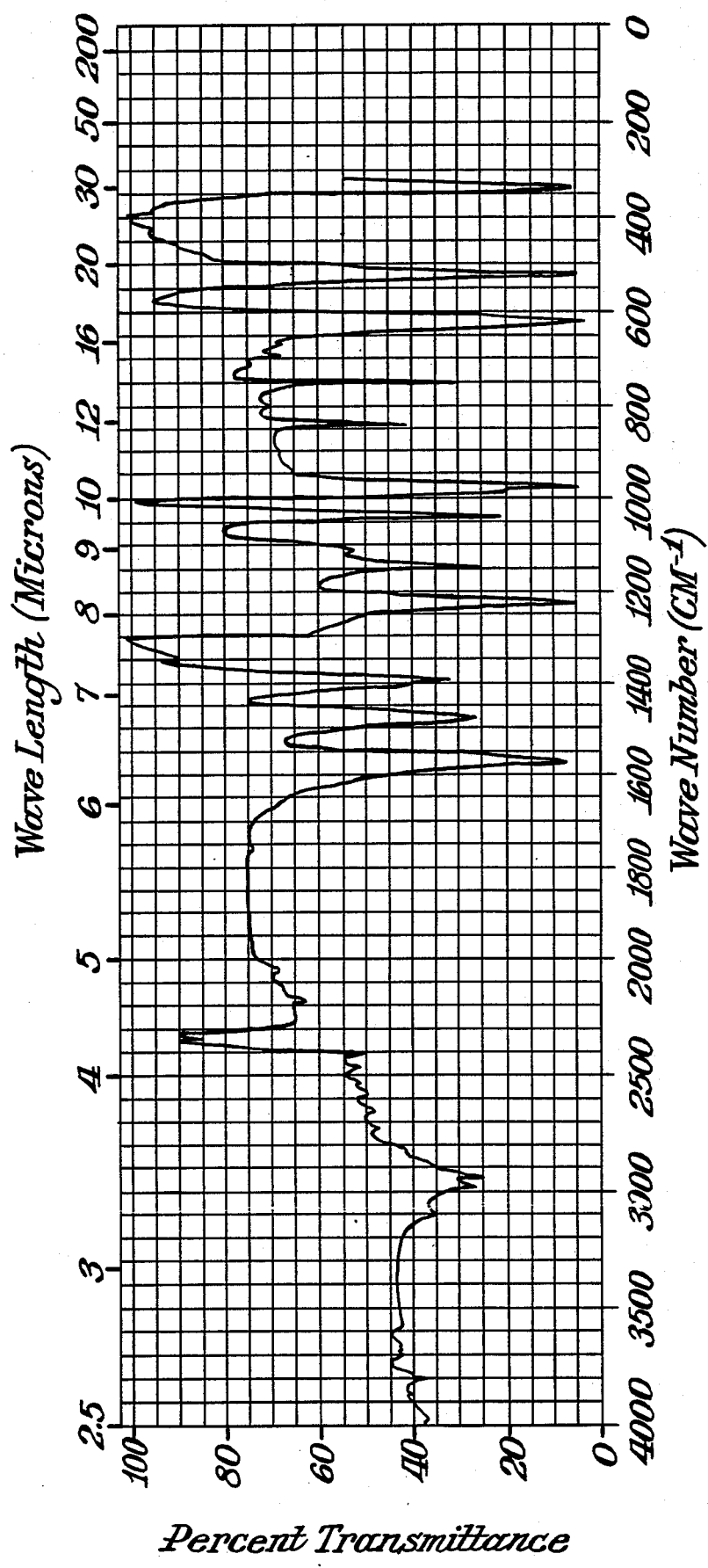
FIG. 2 is a reproduction of the transmittance of Pt(C$_4$H$_8$NO)$_2$Cl$_2$ in a cesium iodide (CsI) pellet.
Figure 3:
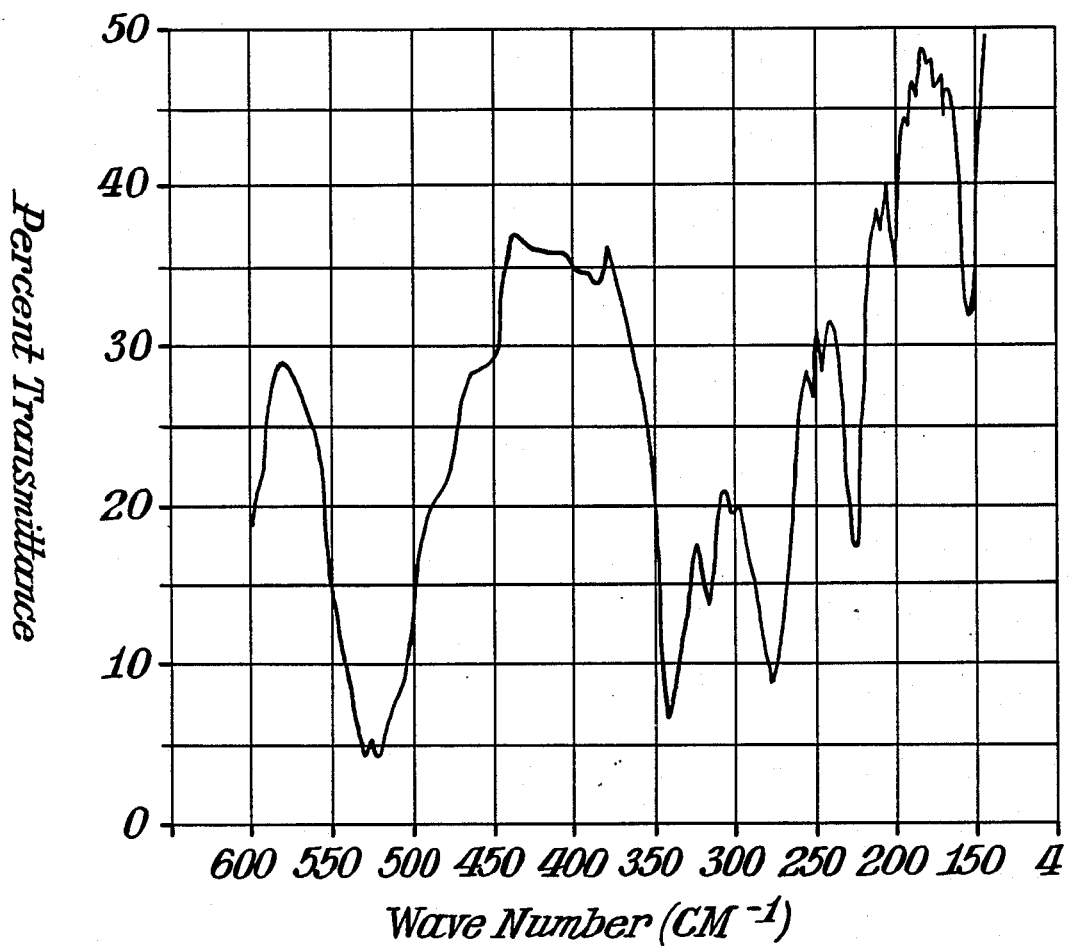
FIG. 3 is a reproduction of the reflectance infrared spectrum of Pt(C$_4$H$_8$NO)$_2$Cl$_2$ in the solid state.

These results are tabulated in the table and shown in FIG. 1, FIG. 2, and FIG. 3. Experimental bands indicated above and in the table, in some cases did not agree with the literature values for DMA. The experimental (O—H) band, for instance, was much stronger indicating water contamination of DMA. Upon distillation of DMA, however, a poorer yield of $Pt(C_4H_8NO)_2Cl_2$ was obtained.

TABLE

| dma Literature (cm$^{-1}$) | dma Experimental cm$^{-1}$ | $Pt(C_4H_8NO)_2Cl_2$ cm$^{-1}$ | Assignment | Reference |
|---|---|---|---|---|
| | | | Infrared Assignment for the Compound $[Pt(CH_2N(CH_3)C(CH_3)O)_2Cl_2]$ | |
| 3500 | 3500 | | (O—H) | (1) |
| 3030 | 3050 | 2975 | γ(C—H) | (1) |
| 2941 | 2930 | 2940 | | |
| 2850 | 2850 | | | |
| 1639 | 1638 | 1568 | γ(C=O) | (1) |
| 1550 | 1538 | | δ(C—H) + | (1) |
| 1492 | 1485 | 1474 | γ(C—N) + | |
| 1398 | 1388 | 1392 | γ(C=N) | |
| 1266 | 1254 | 1227 | | |
| 1190 | 1178 | 1148 | γ(C—O) | (1) |
| 1064 | 1045 | 1034 | | |
| 1015 | 1005 | 970 | | |
| | | 838 | γ(C—N) | (1) |
| | | 751 | | |
| | | 618 | | |
| | | 603 | γ(Pt—C) | (2) |
| | | 503 | | |
| | | 522 | γ(Pt—O) | (3) |
| | | 335 | γ(Pt—Cl) | (3) |

(1) a. Silverstein, R. M., et al. "Spectrophotometric Identification of Organic Compounds," John Wiley, Inc., New York, NY, 1981
b. "The Aldrich Library of Infrared Spectra" Pouchest, C. J. Ed., Milwaukee, WI, 1975
(2) Adams, D. M., et al., J. Chem. Soc. 1960, 2047
(3) Nakamoto, K., et al., "Spectroscopy and Structure of Metal Chelate Compounds," John Wiley & Sons, Inc., New York, NY, 1968, pp. 249-268

STUDIES RELATING TO $(C_4H_9NO)_2PtCl_2$

Studies corresponding to those studies done with the preceding, $(C_4H_8NO)_2PtCl_2$, were conducted on the darker yellow product of the reaction of DMA and $K_2PtCl_4$, a compound more soluble in the reactant-/mother liquor. These studies revealed that the compound of empirical formula $(C_4H_9NO)_2PtCl_2$ is not a chelate and that the amide ligand is bonded to the platinum(II) metal center through the carbonyl oxygen. The amide ligand and the chloride atoms are both in the trans positions with respect to the platinum.

STRUCTURES

The data collected in the foregoing studies of the two reaction products indicate certain structures which appear consistent with theory. However, further consideration had to be given to explain the nature of bonding of these complexes. Structures indicated by these data for the pale yellow, less soluble product

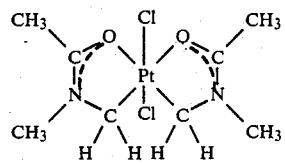

and for the more soluble, darker product

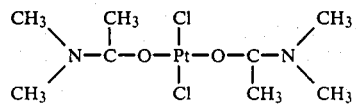

leave the carbonyl carbons of each compound electron deficient. As an approach, consideration was given to a mechanism whereby these structures are formed to explain the properties of each structure and the chemical utility for the chelate.

Organo-platinum(IV) compounds have previously been prepared from suitable platinum(II) complexes by oxidative addition of halogens or alkylating agents (Belluco, V., "Organometallic and Coordination Chemistry of Platinum," Academic Press, Inc., London 1974, pp. 95–107 and 174–208). Mechanically, it appears that both the electrophilic and nucleophilic ends of the reagents attack the metal atom. Dimethyl acetamide can be formulated as such a reagent:

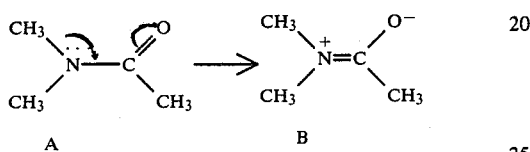

Species B, with nucleophilic and electrophilic sites, could attack the platinum(II) central atom replacing the chloride ion with the oxygen nucleophile, and form the intermediates (chloride ion omitted for clarity):

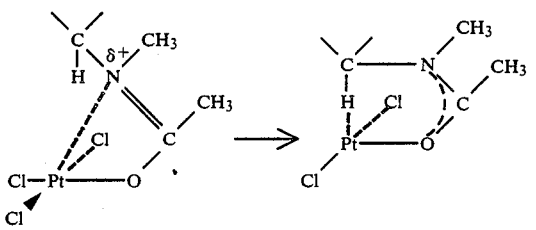

This intermediate has the disadvantage of only four members in the ring, but the advantage of bringing the methyl substitute of the nitrogen electrophile close to the coordination sphere of platinum.

The foregoing mechanistic explanation of an initial step in the reaction process enables fulfillment of valence requirements and accommodates the structural element indicated by X-ray, NMR, and infrared spectroscopic studies.

CHEMICAL REACTIONS

The capacity of metal-organic complexes, particularly chelate compounds, to act as intermediaries to enable simpler routes to compounds which are synthesized only with difficulty was investigated with the cis acetamide-platinum chelate. It was found that in a solvent such as tetrahydrofuran

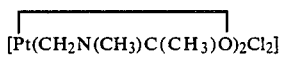

(the chelate of the invention) and benzyl magnesium bromide yield the mixed secondary amide $CH_3C(O)N(CH_3)CH_2C_6H_5$.

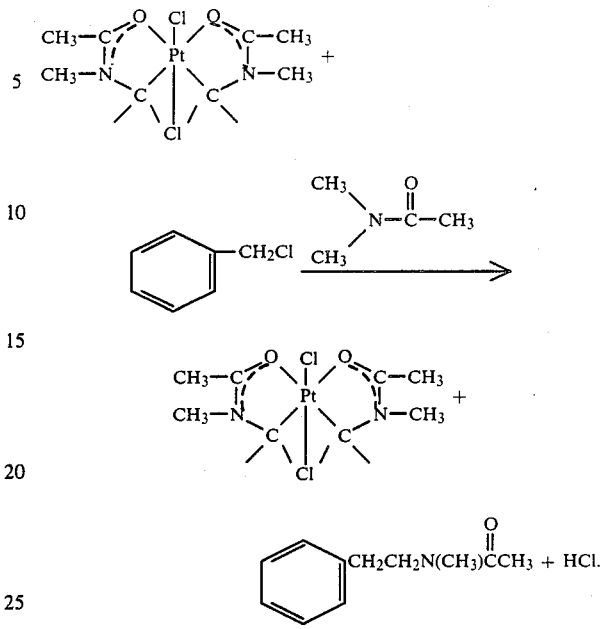

The chloroplatinum amine intermediate interacts with the solvent to regenerate the chelate. The mixed acetamide, methyl-/phenethyl-, upon hydrolysis yields a mixed secondary amine, widely used in synthesis of medicinal compounds by hydrolysis to the corresponding secondary amine.

The chelate of the present invention is useful in preparation Benadryl ®," (Park-Davis-2-diphenylmethoxy-N,N-dimethylethanamine hydrochloride, by a reaction starting with a Grignard reagent:

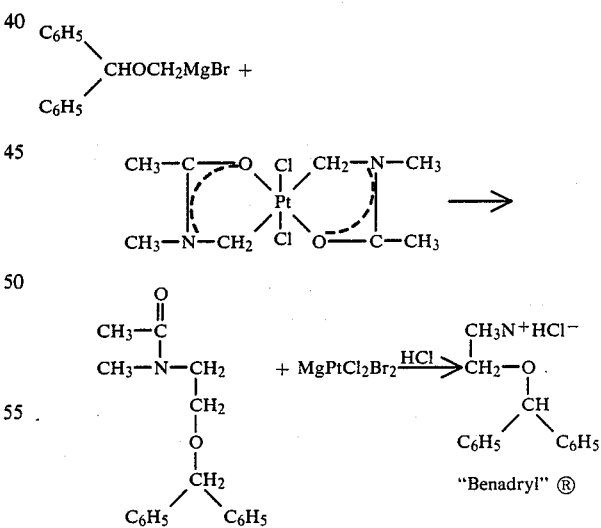

While the foregoing details of the invention relate to preparation of platinum(IV) chelates with amide ligands derived from the reaction of dimethylacetamide and potassium tetrachloroplatinate(II), preparation of analogous chelates from other disubstituted amides is within the scope of the invention. Embraced amides are represented by the general formula:

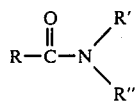

where
R includes H—, CH₃—, CH₃(CH₂)ₙ and aryl(CH₂)ₙ
where n=1-6

R' and R" includes CH₃—, CH₃(CH₂)ₙ and aryl(CH₂)ₙ where n=1-6 and

R' and R" may be the same or different.

It is understood that conditions for preparation of platinum(IV) chelates may depend upon the selected substituted amide, however, adjustment can be made in the procedures as are well known and customary to those skilled in the art. For example, the solubility of the reactant (K₂PtCl₄) and the platinum(IV) chelate varies among the various substituted amides. In the preparation of the dimethylacetamide-derived chelate, a preferred temperature of 60° C. for approximately 120 hours dissolved starting chloroplatinate. This temperature may be varied but temperatures approaching 100° C. are to be avoided since temperatures at this level can cause formation of platinum black. The time and temperature are selected on the basis of the time to dissolve the chloroplatinate.

As an example of preparation of chelates with analogs of dimethylacetamide, diethylacetamide as the source of the amide was used as the reactant-solvent in preparation of the platinum(IV) chelate. The platinum(IV) chelate derived from diethylacetamide, identified by infrared and nuclear magnetic resonance, was separated from the mother liquor as a yellow-brown oil rather than by crystallization as was the chelate from dimethylacetamide.

We claim:

1. A coordination compound of platinum(IV) having the empirical formula

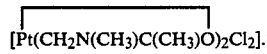

[Pt(CH₂N(CH₃)C(CH₃)O)₂Cl₂].

2. The coordination compound of claim 1 wherein said compound comprises two organic chelated ligands positioned cis to a central axis through the platinum metal center of said structure and two chloride atoms trans to the central axis.

3. The coordination compound of claim 1 having the structural formula

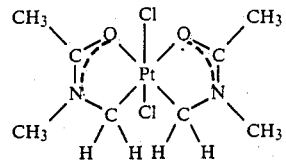

4. A coordination compound wherein said compound is made by a process comprising the steps:
adding potassium tetrachloroplatinate(II) to at least a two-fold molar excess of dimethylacetamide;
heating the resulting mixture to a temperaure below 100° C. until the potassium tetrachloroplatinate(II) dissolves thereby forming potassium chloride and a supernatant liquid;
separating said formed potassium chloride from the supernatant liquid;
reducing the volume of the supernatant liquid until a solid begins to form wherein said solid is said coordination compound; and
separating pale yellow crystals of said solid compound from the supernatant liquid.

5. The coordination compound of claim 4 wherein the molar excess of dimethylacetamide to potassium tetrachlorplatinate(II) is up to 500 and the volume of said supernatant liquid is reduced to one third its initial volume to cause separation of crystals.

6. A composition comprising platinum (IV) chelates comprising amide-derived ligands prepared by a process which includes the reaction of potassium tetrachloroplatinum(II) and n-disubstituted amides selected from the group consisting of

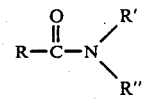

where
R includes H—, CH₃—, CH₃(CH₂)ₙ and aryl(CH₂)ₙ where n=1 to 6 and
R' and R" includes CH₃, CH₃(CH₂)ₙ and aryl(CH₂)ₙ where n=1 to 6, the process comprising the steps of forming a mixture of potassium chloroplatinate(II) and a molar excess of the selected amide as a solvent-reactant, maintaining the mixture at a temperature below 100° C. for a time sufficient to dissolve the potassium chloroplatinate(II) and recovering the platinum(IV) amide-derived chelate from the solvent-reactant.

* * * * *